(12) United States Patent
Herr et al.

(10) Patent No.: US 10,124,064 B2
(45) Date of Patent: Nov. 13, 2018

(54) ANTIMICROBIAL COMPOSITIONS OF AMINOGLYCOSIDIC ANTIBIOTICS AND ZINC ION CHELATORS SPECIFICALLY FORMULATED FOR ENHANCED INHIBITION OF BACTERIAL COLONIZATION AND ANTIBACTERIAL EFFICACY

(71) Applicant: University of Cincinnati, Cincinnati, OH (US)

(72) Inventors: Andrew B. Herr, Cincinnati, OH (US); Gary Young, Hopkinton, MA (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 15/783,509

(22) Filed: Oct. 13, 2017

(65) Prior Publication Data

US 2018/0036410 A1 Feb. 8, 2018

Related U.S. Application Data

(62) Division of application No. 14/254,362, filed on Apr. 16, 2014, now Pat. No. 9,821,063.

(60) Provisional application No. 61/812,701, filed on Apr. 16, 2013.

(51) Int. Cl.
| | |
|---|---|
| *A61K 47/12* | (2006.01) |
| *A61K 31/7036* | (2006.01) |
| *A61K 9/12* | (2006.01) |
| *A61K 9/06* | (2006.01) |
| *A61K 47/02* | (2006.01) |
| *A01N 47/44* | (2006.01) |
| *A01N 37/36* | (2006.01) |
| *A61L 15/46* | (2006.01) |
| *A01N 43/16* | (2006.01) |
| *A61K 9/00* | (2006.01) |
| *A61K 9/70* | (2006.01) |

(52) U.S. Cl.
CPC .............. *A61K 47/12* (2013.01); *A01N 37/36* (2013.01); *A01N 43/16* (2013.01); *A01N 47/44* (2013.01); *A61K 9/0014* (2013.01); *A61K 9/06* (2013.01); *A61K 9/12* (2013.01); *A61K 31/7036* (2013.01); *A61K 47/02* (2013.01); *A61L 15/46* (2013.01); *A61K 9/7015* (2013.01); *A61L 2300/406* (2013.01); *A61L 2300/45* (2013.01)

(58) Field of Classification Search
None
See application file for complete search history.

(56) References Cited

U.S. PATENT DOCUMENTS

| | | | |
|---|---|---|---|
| 5,133,965 A | 7/1992 | Fountain | |
| 5,688,516 A | 11/1997 | Raad et al. | |
| 6,267,979 B1 | 7/2001 | Raad et al. | |
| 2004/0118778 A1 | 6/2004 | Qian et al. | |
| 2004/0151765 A1* | 8/2004 | Ritchie | A61L 15/44 424/445 |
| 2009/0015538 A1 | 6/2009 | Zhang | |
| 2009/0155387 A1* | 6/2009 | Zhang | A61K 9/0019 424/680 |
| 2010/0093652 A1 | 4/2010 | Spring | |
| 2010/0215704 A1 | 8/2010 | Sjodin | |

FOREIGN PATENT DOCUMENTS

| | | |
|---|---|---|
| DE | 19753176 | 7/1999 |
| EP | 2062581 | 5/2009 |
| EP | 20652585 | 5/2009 |
| WO | 1994010838 | 5/1994 |
| WO | 2002024143 | 3/2002 |
| WO | 20090155088 | 12/2009 |
| WO | 2013006837 | 1/2013 |

OTHER PUBLICATIONS

Rennington's Pharmaceutical Sciences, 17th Edition, edited by A. R. Gennaro. Easton, PA: Mack Publishing Company, pp. 324-325. (Year: 1985).*

Walter H. Traub and Birgit Leonhard. Heat stability of the antimicrobial activity of sixty-two antibacterial agents. Journal of Antimicrobial Chemotherapy (1995) 35, 149-154. (Year: 1995).*

* cited by examiner

*Primary Examiner* — Michael P Cohen
(74) *Attorney, Agent, or Firm* — Dinsmore & Shohl LLP

(57) ABSTRACT

Pharmaceutical compositions comprising an aminoglycosidic antibiotic and at least one zinc-chelating agent in a specified concentration, and methods of inhibiting bacterial colonization, biofilm formation and if treating bacterial infections utilizing the compositions are provided. Topical formulations suitable for wound care, and surface-applicable formulations suitable for medical, industrial and household disinfecting needs are also described.

8 Claims, 3 Drawing Sheets

ANTIMICROBIAL COMPOSITIONS OF AMINOGLYCOSIDIC ANTIBIOTICS AND ZINC ION CHELATORS SPECIFICALLY FORMULATED FOR ENHANCED INHIBITION OF BACTERIAL COLONIZATION AND ANTIBACTERIAL EFFICACY

PRIORITY CLAIM

This application is a divisional of U.S. application Ser. No. 14/254,362, filed Apr. 16, 2014, and claims priority under 35 U.S.C. § 119 to U.S. Provisional Application Ser. No. 61/812,701 filed Apr. 16, 2013, each of which is incorporated by reference in its entirety.

TECHNICAL FIELD

The subject matter of the disclosure relates to pharmaceutical compositions effective against resistant bacterial colonies, in particular against *Staphylococcus* and in inhibiting formation of biofilms comprising *Staphylococcus* bacterial cells. The disclosure further relates to topical composition formulations, methods of treating and inhibiting *Staphylococcus* infections utilizing the compositions, and to articles of manufacture including wound dressings, bandages and specialty clothing having the inventive antibacterial compositions infused into the fabric.

BACKGROUND

The incidence of wound infections, especially associated with *Staphylococcus aureus* and *Staphylococcus epidermidis*, is a major concern for healthcare providers. *S. aureus* is one of the more common pathogens found in chronic wounds, and *S. epidermidis* is the most common pathogen associated with device-related infections. Further, *S. pseudintermedius* is a common pathogen associated with recurrent veterinary infections. *S. aureus*, *S. epidermidis*, and *S. pseudintermedius* are known to readily form biofilms, which are surface-adherent bacterial communities that render the bacteria resistant to ordinary antibiotics or host immune responses, and greatly increase healthcare treatment costs.

A leading factor in the pathogenesis of chronic wounds is bacterial infection. Bacteria colonizing wounds can evoke a persistent inflammatory response which is deleterious to the healing process. Cells like neutrophils and macrophages upregulate pro-inflammatory cytokines like IL-1 and TNF-α, which in turn lead to elevated levels of matrix metalloproteinases (MMPs), decreased growth factor expression, and ultimate aberration of the healing process. One of the most common species of bacteria cultured from chronic wounds is *Staphylococcus aureus*, which along with certain other bacterial species, has the ability to encase itself in an extracellular polysaccharide matrix (EPS) called a glycocalyx. Once a population adopts this sessile phenotype, it is substantially more resistant to host defense mechanisms as well as exogenous antimicrobials. Overcoming the protective characteristics of these "biofilms" has proven very difficult and novel effective methods of prevention and treatment are therefore very desirable.

Previous work by the present investigators indicated that zinc is required for the initial formation of staphylococcal biofilms (see, e.g. Conrady D et al. "A zinc-dependent adhesion module is responsible for intercellular adhesion in staphylococcal biofilms" *PNAS* 2008, 105(49):1945661, and U.S. application Ser. No. 12/994,921, the entire disclosures of which are incorporated herein by this reference.) It was shown that diethylenetriamine pentaacetic acid (DTPA), an exemplary zinc chelator, could inhibit biofilm formation by *S. aureus* and *S. epidermidis*. A biophysical characterization of a G5 domain-containing B-repeat region from Aap was disclosed, revealing that it is a zinc ($Zn^{2+}$)-dependent adhesion module ("zinc adhesion module") responsible for intercellular interaction in staphylococcal biofilms. This zinc adhesion module has been identified in a variety of bacteria, including gram positive bacteria generally, and provides a specific target for zinc chelation and biofilm inhibition in biofilms comprised of bacteria having a G5 domain. Zinc chelation was shown to inhibit formation of both *S. epidermidis* and methicillin-resistant *S. aureus* biofilms and supplementation with additional zinc in the physiological range was shown to reverse the effect. Observation of the reversible effect provides a means for identifying bacteria possessing a zinc adhesion module, which can form an adhesive intercellular contact referred to as a "zinc zipper," and underscores the criticality of zinc in intercellular adhesion, providing a specific target for chelation and biofilm inhibition. Furthermore, it was found that addition of a soluble Aap fragment containing a single intact zinc adhesion module inhibits biofilm formation in a dose-dependent manner, indicating that the G5 domain-containing B-repeat region is indeed a required element for intercellular adhesion in staphylococcal biofilms.

Compositions comprising both an antibiotic and a metal ion chelator are known in the art. U.S. application Ser. No. 13/095,262 to Raad et al., along with a portfolio of related art out of the same laboratory, discloses compositions comprising particular antibiotics with EDTA, a well-known iron/calcium chelator. Raad restricts examples and working embodiments to compositions comprising EDTA, and teaches the necessity of alcohol in the compositions; expressly teaching that combinations of antibiotic and EDTA without alcohol require unacceptably long exposure times for desired efficacy. Raad fails to expressly disclose compositions comprising zinc chelators and fails to appreciate mechanistic underpinnings to synergies which may be achieved specifically in combinations with zinc chelators.

The use of zinc chelators in combination with antibiotic compositions is also known. U.S. patent application Ser. No. 12/391,357 to Zhang et al. discloses compositions of aminoglycoside antibiotics and ion chelators generally; however Zhang teaches addition of the ion chelator in extremely small amounts, reflecting the contemplated mechanistic role of the chelator according to Zhang. In particular Zhang teaches that a combination of β-lactam antibiotics with aminoglycoside antibiotics provides an anti-bacterial synergy, but that if dissolved in the same solution, either a salt precipitates out due to an acid-base reaction, or the amino group of the aminoglycoside antibiotic reacts with the β-lactam group of the β-lactam antibiotics, drastically reducing the efficacy of these types of antibiotics and posing potential dangers to patients if the antibiotics are administered as IV solutions. The addition of a chelator according to Zhang prevents the formation of these residual aggregate particles. Zhang did not appreciate or disclose any synergy with respect to antibiotic efficacy of an antibiotic upon addition of a chelator, or with respect to antibiotic efficacy of a chelator upon addition of an antibiotic, and did not disclose antibiotic compositions comprising amounts of chelator sufficient to provide this unexpected synergy.

Hence, there remains a need in the art for antimicrobial compositions effective against biofilms in hospital and industrial settings, and for compositions formulated to provide enhanced antibiotic efficacy in the treatment of wounds.

SUMMARY

Accordingly, the present disclosure provide compositions of an antibiotic and a zinc chelator exhibiting unexpected efficacy against biofilms and biofilm formation, and enhanced antibiotic efficacy in wound care. In particular compositions of antimicrobials and DTPA exhibit surprising synergistic antibiotic efficacy in inhibiting biofilm formation and in dispersing biofilms comprising gram-positive bacteria cells, and in particular Staphalococcus cells, for example S. aureus and S. epidermidis. By introducing DTPA into the environment of S. aureus, S. epidermidis, and S. pseudintermedius, the chelator binds zinc, sequestering it from the bacteria and thereby inhibiting biofilm formation. S. aureus, S. epidermidis, or S. pseudintermedius preserved in the planktonic state are then be more easily targeted and eradicated by traditional, topical antimicrobials. In studies using a porcine wound model the present investigators found that compositions comprising both DTPA and gentamicin formulated for sustained topical contact with a wound exhibited unexpected efficacy against bacterial colonization, with unexpected efficacy occurring at very specific concentrations of DTPA.

One embodiment of the disclosure is directed to pharmaceutical compositions comprising at least one aminoglycosidic antibiotic and at least one metal ion chelating agent, wherein a concentration of metal ion chelating agent is at least about 1 mg/ml. In specific embodiments the chelator is a zinc chelator, and in very specific embodiments the chelator is DTPA in concentrations of at least about 15 mg/ml. A specific aminoglycosidic antibiotic comprises gentamicin or kanamycin, and in very specific embodiments the antibiotic comprises gentamicin.

Other embodiments provide compositions especially formulated for topical application to skin. Such compositions comprise from about 0.05 to about 1% gentamicin by weight, 2.5 to 15 mg/ml DTPA, and an oil-in-water emulsion base designed to keep a wound moist for enhanced healing. Methods for formulating effective compositions for topical application are also provided. Methods for treating wounds utilizing the pharmaceutical compositions are also disclosed, including specific embodiments directed to application of topical formulations to wounds.

Another embodiment relates to methods of inhibiting formation of biofilm on hard surfaces, for example on medical devices, hospital room surfaces, bed rails, floors, and the like. Household consumer embodiments formulated as spray or wipe formulations are also contemplated for general consumer use, for example, for application to toys, nursery surfaces, bathroom surfaces and other commonly contaminated household surfaces. Industrial applications, for example drainage, sewer, and water treatment piping, containment or transport vessels and surfaces may also be treated according to certain embodiments, in particular to inhibit formation of biofilms comprising one or more of S. aureus, S. epidermidis, and S. pseudintermedius cells.

According to further embodiments, textiles or other woven materials may be infused or impregnated with the inventive compositions to provide immediate application to a wound under ordinary or extreme treatment conditions. In a particular embodiment clothing specially designed for military or enforcement personnel may be manufactured from fabrics having at least a portion impregnated with embodiments of the inventive compositions for in situ application to wounds sustained in the field. Other embodiments include wound dressings and bandages impregnated with active combinations according to the disclosure.

An additional embodiment is directed to methods for augmenting the antibacterial efficacy of gentamicin generally where gentamicin has established efficacy or where gentamicin has known resistance. In the case of Staphylococcus biofilms with known resistance to gentamicin, compositions according to embodiments of the invention provide surprising enhanced antibacterial efficacy.

These and other features and aspects of the disclosure will be further elaborated and clarified by reference to the Figures and Detailed Description as set forth herein.

DETAILED DESCRIPTION

Figure 1:
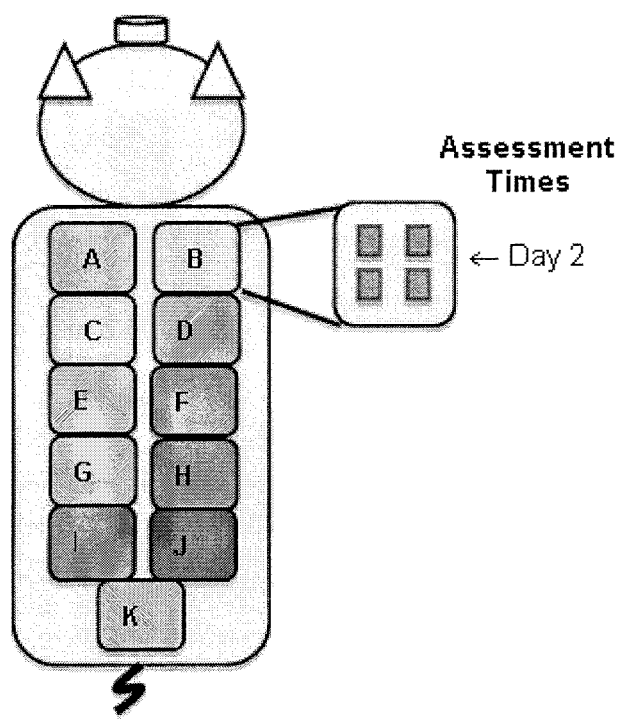
FIG. 1: Pictorial representation of the porcine wound model experimental design; 44 deep partial thickness wounds were made in the peravertebral and thoracic areas of each of two swine and four wounds were randomly assigned to each of the 11 treatment groups.

The present invention provides compositions effective for inhibiting bacterial colonization and formation of biofilms, and having enhanced antibiotic efficacy. Formulations suitable for hard surface and topical skin treatment applications, and formulations suitable for personal care applications, as well as articles impregnated or coated with the inventive compositions and methods utilizing the compositions and articles are also described. Embodiments of the invention are underpinned by the surprising discovery that adding certain specific concentrations of zinc chelating agents to an antimicrobial composition provides a synergistic effect with respect to inhibiting bacterial colonization and biofilm formation and reducing bacterial load. The following definitions apply to construe the scope of terms set forth herein. If a definition is not expressly provided, the scope of a term is construed according to its ordinary meaning in the relevant art.

The term "biofilm" refers to matrix-enclosed microbial accretions to biological or non-biological surfaces. Biofilm formation represents a protected mode of growth that allows cells to survive in hostile environments.

The term "biofilm formation" is intended to include the formation, growth, and modification of the bacterial colonies contained with biofilm structures, as well as the synthesis and maintenance of a polysaccharide matrix of the biofilm structures. Also within the scope of this term is formation of protein-based biofilms that do not secrete polysaccharide in the matrix but which comprise Aap-like proteins which permit bacteria to form a biofilm architecture.

The term "zinc adhesion module" refers to a polypeptide fold found in bacterial cell-surface proteins including, but not limited to, the Accumulation-associated protein (Aap) from Staphylococcus epidermidis. The zinc adhesion module comprises a polypeptide sequence that includes at least one G5 domain, and optionally additional amino acid sequence.

The terms "chelator" or "metal ion chelator" refer to any substance that is able to remove a metal ion from a solution system by forming a new complex ion that has different chemical properties than those of the original metal ion. The term is further intended to encompass substances that are capable of chelating metal ions, specifically divalent metals.

The term "metal ions" is intended to include any metal ion that is bioavailable, i.e., any metal ion involved in a biochemical reaction or pathway, or any metal ion that is available in the fluid, tissue, or bone of a subject.

The term "zinc chelator" refers to any substance that is able to chelate a zinc ($Zn^{2+}$) ion and thus deplete zinc from aqueous environments.

The term "gram positive bacteria" refers to bacteria having cell walls with high amounts of peptidoglycan. Gram positive bacteria are identified by their tendency to retain crystal violet and stain dark blue or violet in the Gram staining protocol.

The term "gram negative bacteria" refers to bacteria having thinner peptidoglycan layers which do not retain the crystal violet stain in the Gram staining protocol and instead retain the counterstain, typically safranin. Gram negative bacteria stain red or pink in the Gram staining protocol.

The term "mammal" refers to organisms within that taxonomic class that can suffer from biofilm-associated states. The term includes humans, for example, as well as wild and domesticated animals and livestock, including but not limited to horses, chimpanzees, macaques, pigs, sheep, goats, hamsters, guinea pigs, monkeys, bears, dogs, cats, mice, rabbits, cattle, squirrels, and rats. The term "pharmaceutical composition" includes preparations suitably safe for administration to mammals, for example, humans.

The term "topical formulation" refers to pharmaceutical compositions suitable for dermal administration to a mammal. Suitable topical pharmaceutical compositions include, but are not limited to, gels, creams, lotions, ointments, tinctures, sprays, and solids. In one embodiment, a topical pharmaceutical composition of the present invention is applied on the outer surface of the skin or in the vicinity of cuts, abrasions, turf burn injuries, lacerations, burns, or puncture wounds in order to treat, prevent, or inhibit the formation of bacterial biofilms.

The term "antimicrobial agent" refers to any substance that kills or prevents the growth of bacteria or other microbes.

The term "antibiotic" refers to a substance that is antagonistic to the growth of microorganisms. Suitable antibiotics may be naturally-occurring, chemically-modified, or synthetically-produced.

The term "surgical rinse" refers to a solution used during surgery to irrigate the site of an implanted medical device, with the intent to prevent initial formation of biofilms in the vicinity of the medical device.

The term "dental rinse" refers to a solution containing one or more zinc chelators used as a mouthwash or rinse to prevent the establishment of oral biofilms that lead to dental caries.

The term "personal cleansing composition" refers to a composition that is used for personal hygiene. Personal cleansing compositions include, but are not limited to, gels, creams, suspensions, colloids, soaps, body washes, shampoos, and the like. In one embodiment, the personal cleansing compositions of the present invention inhibit biofilm-related infections including, but not limited to, community-acquired methicillin-resistant *S. aureus* (CA-MRSA) infection.

The term "hard surface" refers to hard surfaces including, but not limited to, surgical instruments and medical devices, storage tanks, pipelines, trays, containers, walls, floors, countertops, locker room floors, benches, lockers, showers, bathrooms, toilets, water filtration units, household surfaces, nursery items e.g. breast pump components and crib surfaces, toys and other household items and the like.

The terms "inhibit," "inhibiting," and "inhibited" as used herein with respect to biofilm formation, refer to the effect of a zinc chelator in disrupting, dispersing or clearing a biofilm, as well as preventing formation of a biofilm.

The term "effective amount," as used herein with respect to inhibiting biofilm formation, refers to an amount of a zinc chelator in combination with an antibiotic sufficient to achieve the desired inhibitory result.

The term "safe and effective amount" refers to an amount of a zinc chelator in combination with an antibiotic that is effective to inhibit biofilm formation without undue adverse side effects, such as toxicity, irritation, or allergic response, commensurate with a reasonable risk/benefit ration when used in the manner of the invention.

The term "therapeutically effective amount" refers to a sufficient amount of an ingredient to treat disorders, at a reasonable benefit/risk ratio applicable to any medical treatment. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; activity of the specific chelator employed: the specific composition employed; the age, body weight, general health, sex and diet of the patient; the time of administration, route of administration, and rate of excretion of the specific compound employed; the duration of the treatment: drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The acronym CFU stands for colony-forming unit, which is an estimate of viable bacterial or fungal numbers. In contrast, a microscopic count includes all cells, dead and living. CFU is an estimate of viable cells. The appearance of a visible colony requires significant growth of the initial cells plated, and generally it is not possible at the time of counting the colonies to determine if the colony arose from one cell or 1,000 cells. Therefore, the results are given as CFU/mL (colony-forming units per milliliter) for liquids, and CFU/g (colony-forming units per gram) for solids to reflect this uncertainty (rather than cells/mL or cells/g as in a direct count).

Embodiments of the invention provide novel pharmaceutical compositions having enhanced efficacy in inhibiting biofilm formation and enhanced antibacterial efficacy in excess of what one would predict based on the inhibitory and antibacterial efficacy of the components individually. The compositions comprise at least one aminoglycosidic antibiotic and at least one zinc ion chelating agent, wherein a concentration of zinc ion chelating agent is at least about 1 mg/ml. In some embodiments, alcohol is expressly excluded as a component of the composition.

According to specific embodiments, the aminoglycosidic antibiotic is etimicin, gentamicin, tobramycin, amikacin, netilmicin, dibekacin, kanamycin, arbekacin, sagamicin, isopamicin, sisomicin, neomycin, paromoycin, streptomycin, spectinomycin, micronomicin, astromicin, ribostamycin, pharmaceutically acceptable salts or hydrates of any of the preceding, or combinations thereof. In very specific embodiments the aminoglycosidic antibiotic is gentamicin or kanamycin, and in more specific embodiments the aminoglycosidic antibiotic is gentamicin. In certain embodiments, the concentration of antibiotic, including gentamicin, ranges from about 0.01% to about 5%, from about 0.01% to about 1%, from about 0.01% to about 0.5%, from about 0.05% to about 0.5%, from about 0.05% to about 0.1%, from about 0.06% to about 0.1%, from about 0.07% to about 0.1%, from about 0.08% to about 0.1%, from about 0.09% to about 0.1%, and the like. In a very specific embodiment, the concentration of gentamicin is about 0.1% by weight.

The zinc chelating agent may be one or more of diethylenetriamine pentaacetic acid (DTPA), N,N,N'-tetrakis(2-pyridinylmethyl)-1,2-ethanediamine (TPEN), 1,10-phenanthroline, ethylene glycol tetraacetic acid (EGTA), diethyldithiocarbamate (DEDTC), ethylenediamine-N,N'-diacetic acid (EDDA), and salts or hydrates thereof. In specific embodiments the zinc ion chelating agent is DTPA or any ion chelator that chelates zinc to a substantially similar extent in an aqueous environment as DTPA. The zinc chelator may be added to the compositions in a salt or hydrate form, and in specific embodiments may be added as $Na_5DTPA$ or $Na_3CaDTPA$, while in very specific embodiments DTPA may be added as $Na_3CaDTPA$. In some embodiments DTPA may be present in the composition in acidic form and in those embodiments it may be desirable to add a solubilizing agent such as hydrochloric acid (HCl). Other solubilizing agents are well known in the art.

Figure 3:
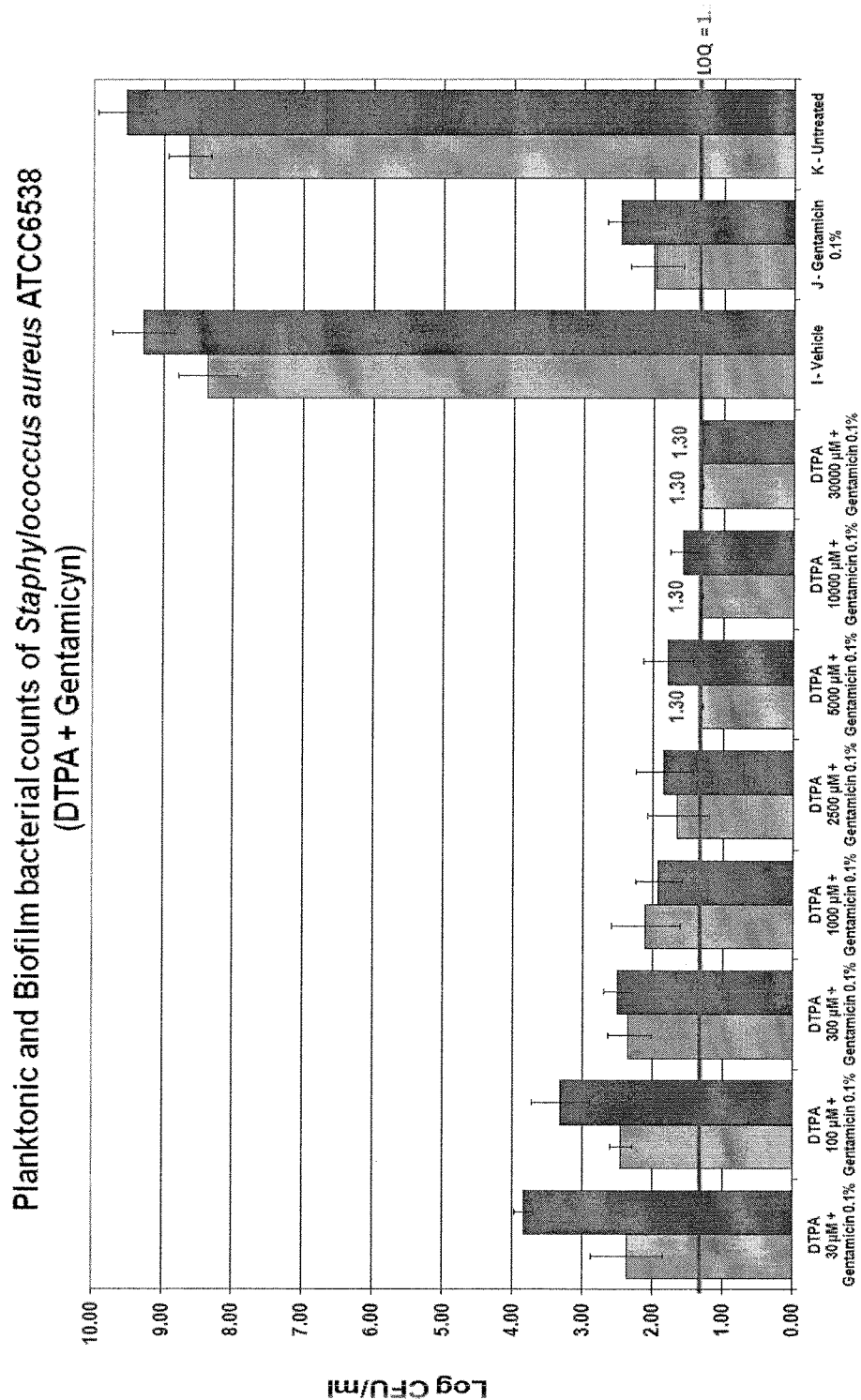
FIG. 3: Bar graph showing planktonic and biofilm Staphylococcus aureus bacterial counts (in log colony forming units per milliliter) as a function of DTPA concentration at constant 0.1% Gentamicin.

The present investigators surprisingly discovered that the amount of zinc chelator present in the composition influences the resulting antibacterial efficacy in an unpredictable way. As illustrated in FIG. 3, at very low concentrations of zinc chelating agent, the antibacterial efficacy of gentamicin is in fact reduced. At increasing concentrations, however, the antibacterial efficacy is enhanced over gentamicin alone, and at even higher concentrations is enhanced in excess of an additive effect demonstrating true positive synergy at particular concentrations. In specific embodiments the concentration of zinc chelating agent is between about 5 mg/ml and 15 mg/ml. At 0.1% by weight formulations of gentamicin, the efficacy appears maximized (no measurable bacterial load) at about 15 mg/ml DTPA; however the concentration of DTPA may be adjusted higher under other conditions, at other antibiotic concentrations and in combination with other antibiotics. In certain embodiments the concentration of zinc chelator may be as high as 50 mg/ml.

In specific embodiments, the concentration of chelator ranges from about 0.5 mg/ml to about 50 mg/ml, or from 1 mg/ml to about 45 mg/ml, or from about 1.5 mg/ml to about 30 mg/ml. In a more specific embodiment, the concentration of chelator ranges from about 2.5 mg/ml to about 15 mg/ml, from about 5 mg/ml to about 15 mg/ml, from about 7.5 mg/ml to about 15 mg/ml, from about 10 mg/ml to about 15 mg/ml, from about 12.5 mg/ml to about 15 mg/ml, and the like. In a very specific embodiment, the chelator is DTPA and the composition concentration is about 30 mM, equivalent to about 15 mg/ml.

Bacterial growth and colonization are inhibited by compositions according to the invention. The bacteria are selected from the group consisting of *Acidothermus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum. Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtheriae, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Finegoldia magna, Geobacillus kaustophilus, Geobacillus thermodenitrificans, Janibacter sp., Kineococcus radiotolerans, Lactobacillus fermentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides sp., Nocardia farcinica, Oceanobacillus iheyensis, Pelotomaculum thermopropionicum, Rhodococcus sp., Saccharopolyspora erythraea*, coagulase-negative *Staphylococcus* species, *Staphylococcus aureus*, methicillin resistant *Staphylococcus aureus* (MRSA), *Staphylococcus epidermidis*, methicillin resistant *Staphylococcus epidermidis*, (MRSE), *Staphylococcus pseudintermedius, Staphylococcus intermedius, Staphylococcus delphini, Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis*, and combinations thereof. According to more specific embodiments, the bacteria are selected from the group consisting of *Corynebacterium urealyticum, Finegoldia magna, Staphylococcus aureus*, methicillin resistant *Staphylococcus aureus* (MRSA), *Staphylococcus epidermidis*, methicillin resistant *Staphylococcus epidermidis* (MRSE), *Streptococcus gordonii, Streptococcus pneumoniae, Streptococcus sanguinis, Streptococcus suis*, and combinations thereof, and in even more specific embodiments the bacteria are selected from the group consisting of *Staphylococcus aureus*, methicillin resistant *Staphylococcus aureus* (MRSA), *Staphylococcus epidermidis*, methicillin resistant *Staphylococcus epidermidis* (MRSE), and combinations thereof.

According to some embodiments of the invention, the composition may be provided as an adherent composition (a composition comprising components intended to increase contact time of the actives with a target surface), a rinse composition, a bath, or formulated as a coating. In specific embodiments the composition is formulated for inhibiting formation of biofilm on a surface. Non-limiting examples of hard surfaces include surgical instruments and medical devices, storage tanks, pipelines, trays, containers, walls, floors, countertops, locker room floors, benches, lockers, showers, bathrooms, toilets, water filtration units, household surfaces, nursery items e.g. breast pump components and crib surfaces, toys and other household items. Other surfaces include textile surfaces, including without limitation clothing, sneakers/shoes, handkerchiefs, utility wear for medical personnel and others exposed to elevated risks of bacterial contamination, diapers, and the like. A surface may also be a body surface, such as skin or other keratin-containing body structures such as nails, hair, fur and hooves. In specific embodiments the surface is contacted with a composition comprising at least one aminoglycosidic antibiotic and at least one zinc ion chelating agent, wherein a concentration of zinc ion chelating agent is at least about 1 mg/ml, and in other specific embodiments is between from about 1 mg/ml to about 15 mg/ml. These methods are particularly effective against biofilms comprising one or more of S. aureus, S. epidermidis, and S. pseudintermedius bacterial cells. In very specific embodiments, the biofilm comprises S. aureus cells.

Contacting may be achieved by spraying, depositing or wiping, and in some aspects a ready-to-use wipe impregnated with compositions according to the invention is provided. In other aspects, spray bottles comprising spray-on compositions are contemplated. Further suitable containment/dispenser and dispensing systems are well-known in the art.

In one aspect of the embodiment, a surgical instrument or medical device is bathed or coated in a composition comprising an antibiotic and an effective amount of at least one zinc chelator. For example, the device may be dipped in the composition and optionally allowed to dry. In another aspect of the embodiment, a device may be sprayed with a composition comprising an antibiotic and an effective amount of at least one zinc chelator and optionally allowed to dry. In a surgical setting, the present method could be used, for example, to bathe a medical device prior to or after implantation prior to closure. Alternatively, a medical device could be coated with a composition comprising an antibiotic and an effective amount of at least one zinc chelator prior to implantation.

Non-limiting examples of implantable medical devices include pacemakers, heart valves, replacement joints, catheters, catheter access ports, dialysis tubing, gastric bands, shunts, screw plates, artificial spinal disc replacements, internal implantable defibrillators, cardiac resynchronization therapy devices, implantable cardiac monitors, mitral valve ring repair devices, left ventricular assist devices (LVADs), artificial hearts, implantable infusion pumps, implantable insulin pumps, stents, implantable neurostimulators, surgical pins/rods/stables, jigs joint replacement devices, maxillofacial implants, and dental implants.

The composition comprising an antibiotic and at least one zinc chelator can be in any form which permits application of the solution to the particular device. In a specific embodiment, the composition is formulated as a gel. In another specific embodiment, the composition is formulated as a foam, and in other specific embodiments the composition may be formulated as a polymer coating. Optionally, the composition may be formulated such that an effective amount of antibiotic and zinc chelator is released gradually, providing for inhibition of biofilm formation over a period of time.

The compositions according to the invention may also be provided as an aspect of personal care formulations, for example as shampoos, nail polish or other nail care products, body wash, soap, surgical scrub, rinse/conditioners, lotions, ointments, dental care products such as mouthwash or toothpaste, or dental cream, make-up foundations, or contained within cosmetic products associated with a known risk of bacterial contamination such as mascara/eye-liner and the like. The key to efficacy for any such formulation is the concentration of zinc chelating agent relative to the antibiotic. In very specific formulations the zinc chelating agent is DTPA, the antimicrobial agent is gentamicin, and the concentration of DTPA is at least 1 mg/ml and from about 0.05 to about 1% gentamicin by weight.

According to other embodiments, the pharmaceutical composition comprising an antibiotic and an effective amount of at least one zinc chelating agent is formulated specifically for topical application to a subject. In specific embodiments the composition comprises at least 1 mg/ml DTPA. In more specific embodiments the composition comprises from about 0.05 to about 1% gentamicin by weight, 2.5 to 15 mg/ml DTPA, and is formulated in an oil-in-water emulsion base. The compositions may be formulated as ointments, creams or lotions. Ointments and creams may, for example, be formulated with an aqueous or oily base with the addition of suitable thickening and/or gelling agents. In certain embodiments, topical compositions may comprise an oil-in-water emulsion as the base. Lotions may be formulated with an aqueous, oily, or emulsion base and may also contain one or more emulsifying agents, stabilizing agents, dispersing agents, suspending agents, thickening agents, or coloring agents. In a very specific embodiment, the composition is a topical pharmaceutical composition comprising about 30 mM (~15 mg/ml) $Na_3CaDTPA$, about 0.1% gentamicin, and an oil-in-water emulsion base.

An illustrative formulation is set forth in Example 3, below. In one specific example described generally, the method comprises providing a base vessel of suitable oil-in-water emulsion base maintained at about 60° C.; preparing an aliquot solution in a first vessel by adding an amount of DTPA to an amount of sterile water and mixing until uniform; transferring a specified volume of the aliquot to a second vessel and adding gentamicin sulfate while mixing until the gentamicin sulfate is substantially fully dissolved; heating the base in the base vessel to about 90° C. while stirring; filtering and transferring the entire contents of the second vessel to the base vessel; mixing until uniform; cooling to about 55° C.; transferring to a sterilization vessel and sterilizing.

Compositions formulated for topical application are particularly useful for treatment of wounds and surgical incisions. "Treatment" is construed to include inhibiting growth of bacteria, inhibiting formation of bacterial colonies and biofilms, as well as antibacterial efficacy. It should be noted that a zinc-chelating agent alone is not considered bactericidal; however it acts to prevent colonization of bacterial cells and formation of biofilms. In combination with an antibiotic, for example gentamicin, both the bacterial colonization and bacterial count appear to be reduced indicating enhanced inhibition of colonization/biofilm formation as well as enhanced bactericidal activity of the composition as a whole. In specific embodiments, the topical formulations are useful for preventing infection in recent wounds and incisions.

Other embodiments provide articles of manufacture such as wound dressings and bandages comprising at least a portion impregnated or coated with a pharmaceutical composition comprising at least one aminoglycosidic antibiotic and at least one zinc ion chelating agent, wherein a concentration of zinc ion chelating agent is between from about 1 mg/ml to about 15 mg/ml. In one aspect the article is an item of clothing worn by a subject engaged in high mortal risk activity such as military or police enforcement activities. In the event of a wound, clothing impregnated with the composition may be pressed into the open wound to inhibit or prevent infection.

In some embodiments between about 5 and 15 mg/ml zinc chelating agent may be added to a composition of an antibiotic, for example, gentamicin, to augment the antibiotic activity of gentamicin. In specific examples the zinc chelating agent comprises DTPA.

The following Examples are set forth to illustrate specific embodiments and aspects of the invention and should not be construed as limiting the full scope of the invention as defined by the claims.

EXAMPLES

Example 1

This example illustrates unexpected antibacterial efficacy of compositions according to the invention. In a very specific exemplary embodiment, the present investigators discovered unexpected positive synergy in the effects of a novel antibiotic-zinc chelator formulation, and in particular gentamicin-DTPA formulations on wounds infected with *S. aureus*. Summarily, forty-four deep, partial-thickness wounds were created on the paravertebral area on two pigs. Four wounds each were randomly assigned to eleven treatment groups and inoculated with *S. aureus* ATCC 6538. Wounds were treated with approximately 200 mg of each treatment. On day 2, wounds were assessed using a flush and scrub technique to recover planktonic and biofilm-associated bacterial count, respectively. All treatment groups at differing concentrations of DTPA alone reduced bacterial counts (planktonic and biofilm) as compared to untreated control wounds. The highest concentration of DTPA (30000 μM) alone showed the largest reduction of both planktonic and biofilm bacteria counts as compared to other DTPA concentrations. DTPA at 5000, 10000 and 30000 μM concentrations when combined with Gentamicin showed a 99.99% reduction of *S. aureus* planktonic bacterial count as compared to untreated wounds. The highest concentration of DTPA (30000 μM) combined with Gentamicin also showed the highest percentage of reduction (99.99%) in *S. aureus* biofilm bacteria counts compared to untreated wounds. This example demonstrates that DTPA, at concentrations of 2500 to 30000 μM, in combination with Gentamicin showed a reduction in both planktonic and biofilm-associated *S. aureus* as compared to Gentamicin alone, indicating a strong synergistic effect of this compound with this antibiotic at specific concentrations of DTPA. This is particularly surprising and unpredicted in view of the data indicating a negative synergy at very low concentrations of DTPA.

Materials and Methods

Swine (2 animals) were used as the experimental animal due to the morphological, physiological, and biochemical similarities between swine skin and human skin.

Animal Wounding:
  44 deep partial thickness wounds measuring 10 mm×7 mm×0.5 mm were made in the peravertebral and thoracic areas of each animal
  4 wounds were randomly assigned to each of the 11 treatment groups Inoculation:
  25 μl of inoculum of $10^6$ CFU/ml were inoculated into each wound and scrubbed lightly using a sterile Teflon spatula.

Experimental Design:
Pig 1: Treatment Groups
  A. 30 μM DTPA
  B. 100 μM DTPA
  C. 300 μM DTPA
  D. 1000 μM DTPA
  E. 30 μM DTPA+Gentamicin 0.1%
  F. 100 μM DTPA+Gentamicin 0.1%
  G. 300 μM DTPA+Gentamicin 0.1%
  H. 1000 μM DTPA+Gentamicin 0.1%
  I. Vehicle
  J. Gentamicin 0.1%
  K. Untreated
Pig 2: Treatment Groups
  A. 2500 μM DTPA
  B. 5000 μM DTPA
  C. 10000 μM DTPA
  D. 30000 μM DTPA
  E. 2500 μM DTPA+Gentamicin 0.1%
  F. 5000 μM DTPA+Gentamicin 0.1%
  G. 10000 μM DTPA+Gentamicin 0.1%
  H. 30000 μM DTPA+Gentamicin 0.1%
  I. Vehicle
  J. Gentamicin 0.1%
  K. Untreated FIG. 1 illustrates the Experimental Design and depicts a schematic diagram of treatment groups and animal wounding Treatment Application:
  Within 20 minutes of inoculation each wound was treated with the appropriate treatment. Each wound was treated with ≅200 mg of the appropriate treatment (days 0 and 1).
  All wounds were covered with polyurethane film dressings Wound Recovery:
  A sterile surgical steel cylinder (22 mm inside diameter) was placed over the wound area and 1 ml of all-purpose neutralizer solution was pipetted inside.
  The site was gently flushed by pipetting in and out three times to remove the loosely attached bacteria (a), this aliquot represents the planktonic bacteria.
  The same wound was then encircled using another sterile cylinder and 1 ml of all-purpose neutralizer solution was again pipetted into the cylinder and this time scrubbed with a sterile Teflon spatula for 30 seconds to remove the firmly attached bacteria (b), this aliquot was aspirated and represents biofilm bacteria.

Bacterial Quantification:
  Serial dilutions (c) were made and quantified using the Spiral Plater System (d) (which deposits a defined amount (50 μl of suspension over the surface of a rotating agar plate).
  *Staphylococcus aureus* was grown on differential and selective medium Mannitol Salt Agar (e) at 37±2° C. for 24 hours.

B. Results

Wounds Treated with DTPA Alone:
  The wounds treated with 30000 μM DTPA contained the lowest counts of *S. aureus* compared to all other concentrations of DTPA.
  Treatment with this concentration resulted in a 99.96% reduction compared to the untreated group.
  Increases in DTPA concentration were directly proportional to the increases in the percentage of both planktonic and biofilm bacterial reduction.
  All wounds, with the exception of those treated with 30 μM DTPA, contained more *S. aureus* in the biofilm phenotype than in a planktonic state.
  The 0.1% Gentamicin positive control produced substantially more reduction in wound bioburden than any of the DTPA concentrations alone.

Figure 2:
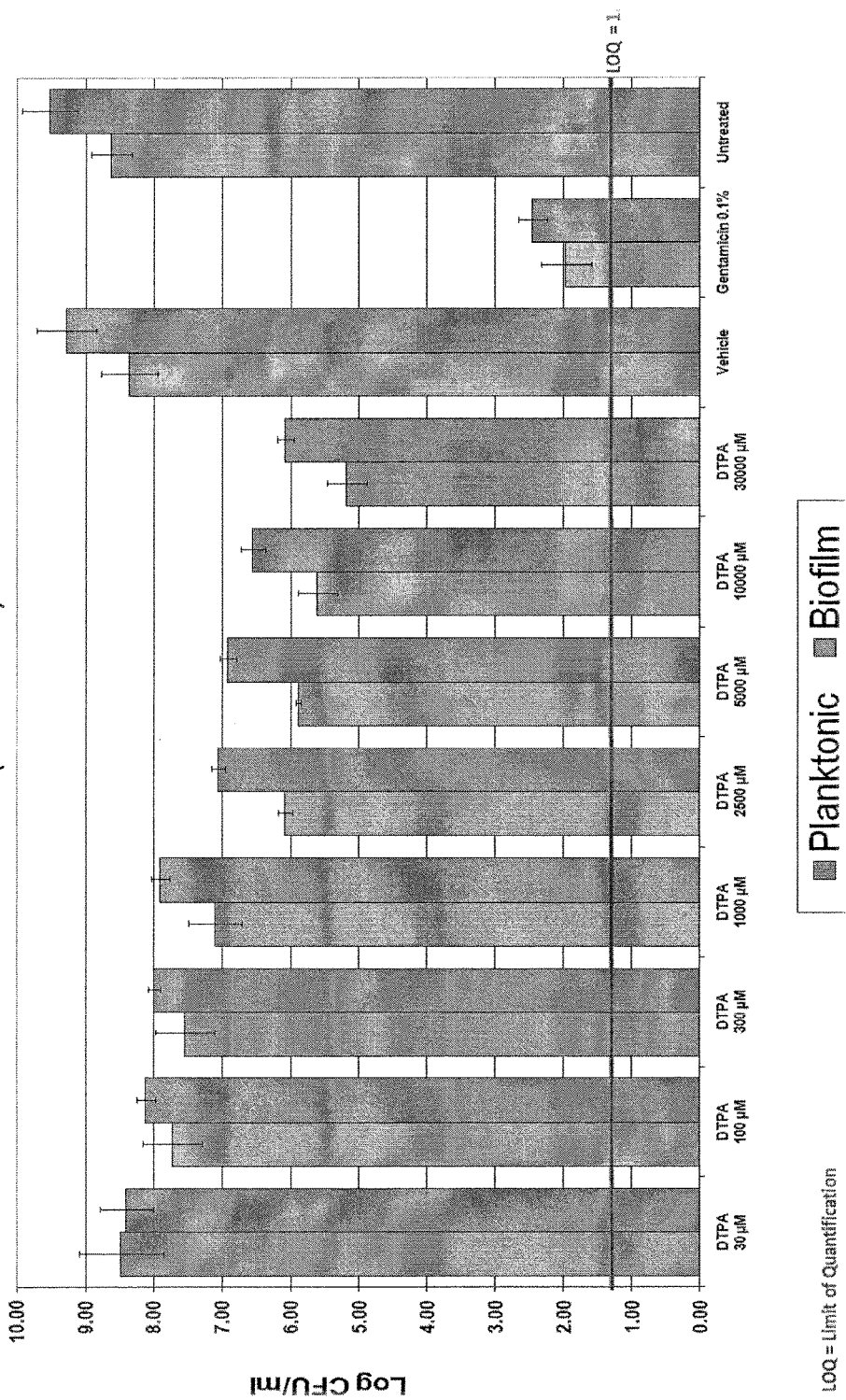
FIG. 2: Bar graph showing planktonic and biofilm Staphylococcus aureus bacterial counts (in log colony forming units per milliliter) as a function of DTPA concentration alone, compared to three treatment controls: vehicle, 0.1% Gentamicin, and untreated.

FIG. 2 provides a bar graph summary for ease of comparison showing wounds treated with DTPA alone in increasing concentrations and the effect on both planktonic and biofilm bacterial counts of S. aureus ATCC6538

Wounds Treated with DTPA/Gentamicin Combination:

The lowest planktonic S. aureus counts were seen in wounds treated with 5000, 10000, and 30000 µM DTPA+Gentamicin 0.1% Compared to the untreated wounds, all three concentrations reduced bioburden by 99.99% to levels below the limit of quantification.

The 30000 µM DTPA+Gentamicin 0.1% resulted in the lowest amount of bacteria in the biofilm phenotype, reducing counts to below the limit of quantification.

Reductions of planktonic and biofilm bacteria were directly proportional to the concentrations of DTPA used.

All wounds, with the exception of those treated with 1000 µM DTPA+Gentamicin 0.1% or 30000 µM DTPA+Gentamicin 0.1%, contained more S. aureus in the biofilm phenotype than in the planktonic state. The exceptions had equally low (undetectable) levels in both biofilm and planktonic state.

The 2500 µM, 5000 µM, 10000 µM, and 30000 µM DTPA+Gentamicin 0.1% treatments all resulted in both planktonic and biofilm counts lower than in the wounds treated with only Gentamicin 0.1%.

Notably, it appears that the addition of very low concentrations of DTPA to Gentamicin actually resulted in a decrease in overall antibiotic efficacy of the composition. i.e. predicting a negative synergy, which unexpectedly reverses to a positive synergy at increasing concentrations of DTPA relative to Gentamicin.

FIG. 3 sets forth a bar graph summary of wounds treated with a DTPA/Gentamicin combination at increasing concentrations of DTPA and the effect on planktonic and biofilm bacterial counts of S. aureus ATCC6538

As is readily apparent from the data, the increased reduction of S. aureus within wounds was directly proportional to the increased concentration of DTPA (with and without Gentamicin 0.1%). The 30000 µM (=15 mg/ml) concentration of DTPA used alone produced a planktonic bacterial count of 5.19±0.29 Log CFU/ml and a biofilm count of 6.09±012 Log CFU/ml, whereas 30000 µM DTPA used in conjunction with Gentamicin 0.1% resulted in wounds containing planktonic and biofilm bacterial loads below the level of quantification (1.30 Log CFU/ml). These were over a 3.89±0.29 and 4.79±01.2 Log differences in colony forming units per milliliter, respectively. The 2500 µM, 5000 µM, 10000 µM, and 30000 µM DTPA (equivalent to 1.25, 2.5, 5 and 15 mg/ml respectively)+Gentamicin 0.1% treatments produced larger reductions in planktonic and biofilm bacterial counts of S. aureus than the Gentamicin 0.1% alone. These data indicate that the zinc chelator, DTPA, has an antimicrobial effect that is synergistic when used in combination with Gentamicin.

Example 2

This example illustrates an exemplary spray formulation of embodiments of the inventive compositions. Essential components comprise from about 15 mg/ml to about 50 mg/ml (30 to 100 mM) DTPA, 0.1% gentamicin, buffering agent (to maintain pH), and optionally one or more excipients such as viscosity modifiers and/or preservatives. The appropriate excipients and suitable concentrations would be readily apparent to a person of ordinary skill in the composition formulating arts. The basic formulation can be adjusted to provide aqueous spray compositions of varying concentrations of DTPA. Methods for preparing the above compositions can be scaled up using methods commonly known in the pharmaceutical arts.

Example 3

This example illustrates an exemplary topical cream formulation.

The topical formulation:

1. Provides an oil-in-water emollient cream/vehicle which will carry and disperse the active pharmaceutical components of DTPA and Gentamicin, along with additional pharmaceutical components which may be included in alternative embodiments;
2. Provides an emulsifier which will keep the active pharmaceutical components evenly dispersed;
3. Provides an emollient cream which acts as carrier (dispersing agent), moisturizer, and humectant (keeps skin soft), preventing water loss and locking in moisture while keeping the site-specific area moist, thus providing a moist environment for enhanced natural wound healing.
4. Provides a topical, emollient cream which, upon contact with a mammalian wound or surgical incision, will evenly and rapidly disperse the active pharmaceutical ingredients into the site-specific application, while being rapidly absorbed into that specific site;

Select GRAS (generally recognized as safe) components were incorporated and pharmaceutically compounded within set parameters, such as timely ingredient additions, temperature, cooling and so forth, such incorporation being well within the skill of an ordinary practitioner.

Select GRAS Ingredients and Their Respective Functions:

1. Glyceryl Stearate/PEG-100: emulsifier
2. Lanolin Alcohol: emulsifier, emollient and viscosity enhancer
3. Cetyl Alcohol: emulsifier, emollient, thickening agent and moisturizer
4. Mineral Oil: emollient
5. Sorbitol 70% Solution: humectant and skin conditioner
6. Purified Water: acts as a carrier and dispersing agent Emulsifiers generally encourage the suspension of one liquid into another, while emollients act as moisturizers to keep the skin (wound) soft, while increasing the skin's ability to hold water and lock in moisture, while lubricating the skin (wound). Providing the ability to keep the wound moist creates an optimal wound healing environment.

The following tabled ingredients illustrate a very specific embodiment of a composition suitable as the cream base for the instant topical formulation.

TABLE 1

Cream Base

| | Component | Amount |
|---|---|---|
| 1 | Glyceryl stearate/PEG-100 (25F-D stearate) | 109.6 g |
| 2 | Lanolin alcohol powder | 12.146 g |
| 3 | Cetyl alcohol powder | 6.122 g |
| 4 | Mineral oil | 7.565 mL |
| 5 | Sorbitol 70% solution | 8.556 mL |
| 6 | Distilled water | 348.3696 mL |

Formulation Instructions:

1. In a suitably sized glass beaker, fitted with a magnetic stirring bar, add the water and sorbitol and mix until uniform.

2. Transfer the solution from step 1 through a 0.22 micron filter into an appropriately sized glass vial.
3. In a separate glass beaker add the following ingredients and initiate heating to 70° C., glycerol stearate/PEG-100 alcohol, lanolin alcohol, cetyl alcohol, and mineral oil.
4. Take the solution from step 3, place in a vial, stopper, seal, and dry heat sterilize overnight at 121 C.
5. In the aseptic suite, utilizing the aseptic hood, place the solution from step 4 into a beaker fitted with a magnetic stirring bar and heat to approximately 90° C.
6. Heat the solution from step 2 to approximately 90° C. and transfer into the solution from step 5, initiate mixing.
7. Heat the mixture, in step 6, to 90° C., discontinue heating and allow to cool to 60° C.
8. Hold solution at 60° C. until further needed.

TABLE 2

Chelating agent - 10 mg/mL solution

| | Component | Amount |
|---|---|---|
| 1 | Na3CaDTPA | 0.5 g |
| 2 | Sterile water for injection | 50 mL |

Formulation Instructions:
1. In a suitably sized glass beaker fitted with a magnetic stirring bar add the Na$_3$CaDTPA.
2. QS with sterile water for injection, initiate mixing, mix until dissolved.

TABLE 3

Topical Composition - 1000 μM chelator/0.1% gentamicin cream

| | Component | Amount |
|---|---|---|
| 1 | Chelating agent, 10 mg/mL solution | 3.221 mL |
| 2 | Sterile water for injection | 2.279 mL |
| 3 | Gentamicin sulfate powder | 0.08 g |
| 4 | Cream base | 45 mL |

Formulation Instructions:
1. Utilizing a suitably sized glass beaker, prepare a secondary aliquot solution by adding the specified quantity of chelating agent solution to the specified amount of sterile water.
2. Place a magnetic stirring bar in the solution and mix until uniform.
3. Utilizing a suitably sized syringe, withdraw 5 mL of the solution from step 2.
4. Discharge the contents into a suitably sized glass beaker fitted with a magnetic stirrer.
5. Initiate mixing at slow speed and add the gentamicin sulfate and mix until dissolved.
6. Reload the syringe with the material in step 5, in a manner to assure total transfer.
7. In a separate suitably sized glass beaker add the cream base which has been maintained at 60° C. and heat to 90° C.
8. Add a magnetic stirring bar to the cream base and initiate mixing at slow speed.
9. Attach a 0.22 micron filter to the syringe holding the 5 mL aliquot from step 6 and transfer the aliquot to the cream base in step 8.
10. Continue mixing until uniform and allow the cream to cool to approximately 55° C. and transfer required amounts into appropriate container.
11. Sterilize.

The above formulation can be readily adjusted to provide topical compositions of varying concentrations of DTPA including, for example, compositions comprising from about 30 μM to about 30 mM DTPA. Optionally, the antibiotic may be omitted. Methods for preparing the above compositions can be scaled up using methods commonly known in the pharmaceutical arts.

Those skilled in the art will recognize, or be able to ascertain using no more than routine experimentation, many equivalents to the specific embodiments of the invention described herein. The scope of the present invention is not intended to be limited to specific examples described in the above Description, but rather is as set forth in the appended claims. In accordance with the claims, articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more elements, limitations, clauses, or descriptive terms, found in any other claim that is dependent on the same base claim. Furthermore, where the claims recite a product (e.g., an article of manufacture or device), it is to be understood that methods of using the product according to any of the methods disclosed herein, and methods of making the product, are included within the scope of the invention, unless otherwise indicated or unless it would be evident to one of ordinary skill in the art that a contradiction or inconsistency would arise. Methods of treating a subject can include a step of providing a subject in need of such treatment (e.g., a subject who has a wound or other medical need for antimicrobial treatment, including a prophylactic need), a step of diagnosing a subject as having such disease or disorder, a step of selecting a subject for treatment, and/or a step of suggesting an article, composition or kit of the invention to a subject or prescribing an article, composition or kit of the invention for a subject or providing instructions regarding use of the article, composition or kit, e.g., instructions for using the article, composition or kit for one or more purposes.

Where elements are presented as lists, it is to be understood that each subgroup of the elements is also disclosed, and any element(s) can be removed from the group. The invention provides all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included.

Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. In addition, any particular embodiment, aspect, element, feature, etc., of the present invention may be explicitly excluded from any one or more of the claims.

What is claimed:

1. A method of formulating a pharmaceutical composition comprising about 0.1% gentamicin by weight and about 5 to 15 mg/ml diethylenetriamine pentaacetic acid (DTPA) as a topical formulation, the method comprising: providing a base vessel of suitable oil-in-water emulsion base maintained at about 60° C.; preparing an aliquot solution in a first vessel by adding an amount of DTPA to an amount of sterile water and mixing until uniform; transferring a specified volume of the aliquot to a second vessel and adding gentamicin sulfate while mixing until the gentamicin sulfate is substantially fully dissolved; heating the base in the base vessel to about 90° C. while stirring; filtering and transferring the entire contents of the second vessel to the base vessel; mixing until uniform; cooling to about 55° C.; transferring to a sterilization vessel and sterilizing.

2. The method according to claim 1, wherein the pharmaceutical composition is in the form of an ointment, a cream, or a lotion.

3. The method according to claim 1, wherein the DTPA is $Na_5DTPA$ or $Na_3CaDTPA$.

4. The method according to claim 1, wherein the DTPA is $Na_3CaDTPA$.

5. The method according to claim 1, wherein the oil-in-water emulsion base further comprises one or more of a thickening agent, a gelling agent, an emulsifying agent, a stabilizing agent, a dispersing agent, a suspending agent, or a coloring agent.

6. The method according to claim 1, wherein the oil-in-water emulsion base comprises glyceryl stearate/PEG-100, lanolin alcohol powder, cetyl alcohol powder, mineral oil, sorbitol 70% solution, and distilled water.

7. The method according to claim 6, wherein providing an oil-in-water emulsion base comprises the steps of:
    (a) combining the distilled water and the sorbitol 70% solution in a first receptacle and mixing until uniform;
    (b) filtering the solution of step (a);
    (c) combining the glyceryl stearate/PEG-100, lanolin alcohol powder, cetyl alcohol powder, and mineral oil in a second receptacle and heating to about 70° C.;
    (d) sterilizing the solution of step (c) by dry heat;
    (e) heating the solution of step (d) to about 90° C. under sterile conditions;
    (f) heating the solution of step (b) to about 90° C. under sterile conditions;
    (g) adding the solution of step (f) to the solution of step (e) and mixing to combine; and
    (h) cooling the solution of step (g) to about 60° C. to provide an oil-in-water emulsion base.

8. A method of treating a wound in a subject, the method comprising topically applying to the wound a pharmaceutical composition comprising about 0.1% gentamicin by weight, about 5 to 15 mg/ml diethylenetriamine pentaacetic acid (DTPA), and an oil-in-water emulsion base.

* * * * *